(12) United States Patent
Chen et al.

(10) Patent No.: US 11,311,692 B2
(45) Date of Patent: *Apr. 26, 2022

(54) NEGATIVE-PRESSURE ORAL APPARATUS AND METHOD FOR MAINTAINING NEGATIVE ORAL PRESSURE AND COLLECTING LIQUID

(71) Applicant: Somnics, Inc. (Taiwan), Zhubei (TW)

(72) Inventors: Chung-Chu Chen, Zhubei (TW); Te-Yang Shen, Sinfong Township (TW)

(73) Assignee: Somnics, Inc., Zhubei (TW)

( * ) Notice: Subject to any disclaimer, the term of this patent is extended or adjusted under 35 U.S.C. 154(b) by 749 days.

This patent is subject to a terminal disclaimer.

(21) Appl. No.: 16/136,698

(22) Filed: Sep. 20, 2018

(65) Prior Publication Data

US 2019/0015618 A1     Jan. 17, 2019

Related U.S. Application Data

(63) Continuation of application No. 15/057,926, filed on Mar. 1, 2016, now Pat. No. 10,080,855, which is a
(Continued)

(30) Foreign Application Priority Data

May 20, 2008    (TW) ................................ 097118459
Jun. 6, 2008    (TW) ................................ 097121064

(51) Int. Cl.
*A61F 5/56*      (2006.01)
*A61M 1/00*     (2006.01)
(Continued)

(52) U.S. Cl.
CPC ........... *A61M 16/0488* (2013.01); *A61F 5/56* (2013.01); *A61F 5/566* (2013.01); *A61M 1/0023* (2013.01);
(Continued)

(58) Field of Classification Search
CPC . A61F 5/56; A61F 5/566; A61C 17/00; A61C 17/04; A61C 17/043; A61C 17/046;
(Continued)

(56) References Cited

U.S. PATENT DOCUMENTS 2,937,445 A    5/1960   Erickson
3,520,300 A    7/1970   Flower, Jr.
(Continued)

FOREIGN PATENT DOCUMENTS

TW    200507818     3/2005
TW    200744551    12/2007
(Continued)

*Primary Examiner* — Keri J Nelson
(74) *Attorney, Agent, or Firm* — Stinson LLP

(57) ABSTRACT

The present invention discloses a negative-pressure oral apparatus capable of relieving discomfort of soft tissues in the oral cavity and improving fixation of the oral apparatus to prevent the oral apparatus from falling off due to mouth opening. The oral apparatus is compact and elastic so that it fits various shapes and sizes of the oral cavity and is easy to be put on and taken off to provide convenience and safety to the user. In another embodiment, a method for maintaining a negative oral pressure and collecting liquid by coupling the oral apparatus to a liquid collecting apparatus capable of effectively providing the oral cavity with a negative pressure to expel liquid in the oral apparatus and deliver the liquid to an absorbing element in the liquid collecting apparatus so as to prevent liquid leakage or contamination.

27 Claims, 14 Drawing Sheets

Related U.S. Application Data continuation of application No. 12/207,841, filed on Sep. 10, 2008, now Pat. No. 9,339,620.

(51) Int. Cl.
*A61M 16/04* (2006.01)
*A61M 16/00* (2006.01)
*A61C 17/06* (2006.01)

(52) U.S. Cl.
CPC .............. *A61M 1/73* (2021.05); *A61M 1/732* (2021.05); *A61M 1/74* (2021.05); *A61M 1/81* (2021.05); *A61M 16/0009* (2014.02); *A61M 16/0493* (2014.02); *A61C 17/06* (2019.05); *A61M 1/0001* (2013.01); *A61M 1/78* (2021.05); *A61M 2016/0027* (2013.01); *A61M 2205/0266* (2013.01); *A61M 2205/0288* (2013.01); *A61M 2205/18* (2013.01); *A61M 2205/3334* (2013.01); *A61M 2205/3344* (2013.01); *A61M 2205/502* (2013.01); *A61M 2210/0631* (2013.01); *A61M 2210/0637* (2013.01)

(58) Field of Classification Search
CPC ....... A61C 7/08; A61M 16/0488; A61M 1/00; A61M 1/0001; A61M 1/0023; A61M 1/0058; A63B 71/085
USPC ..... 128/848, 859, 861, 862, 205.19, 206.22, 128/206.29, 207.14; 433/6, 91–96
See application file for complete search history.

(56) References Cited

U.S. PATENT DOCUMENTS

| | | |
|---|---|---|
| 4,304,227 A | 12/1981 | Samelson |
| 4,676,240 A | 6/1987 | Gardy |
| 5,203,699 A | 4/1993 | McGuire |
| 5,373,859 A * | 12/1994 | Forney .................... A61F 5/566 |
| | | 128/846 |
| 5,692,523 A | 12/1997 | Croll et al. |
| 5,876,199 A | 3/1999 | Bergersen |
| 5,947,133 A | 9/1999 | Kossak |
| 6,494,209 B2 | 12/2002 | Kulick |
| 6,893,259 B1 | 5/2005 | Reizenson |
| 9,339,620 B2 | 5/2016 | Chen et al. |
| 10,080,855 B2 * | 9/2018 | Chen .................... A61F 5/56 |
| 2003/0208149 A1 | 11/2003 | Coffey |
| 2004/0103905 A1 | 6/2004 | Farrell |
| 2005/0166928 A1 | 8/2005 | Jiang |
| 2005/0217678 A1 | 10/2005 | McCormick et al. |
| 2006/0096600 A1 | 5/2006 | Witt et al. |
| 2009/0012441 A1 | 1/2009 | Mulligan |
| 2009/0120446 A1 | 5/2009 | Vaska et al. |
| 2011/0220124 A1 | 9/2011 | Vaska et al. |
| 2014/0034064 A1 | 2/2014 | Chen et al. |

FOREIGN PATENT DOCUMENTS

| | | |
|---|---|---|
| WO | 9949925 A1 | 10/1999 |
| WO | 2006050277 A2 | 5/2006 |

* cited by examiner

NEGATIVE-PRESSURE ORAL APPARATUS AND METHOD FOR MAINTAINING NEGATIVE ORAL PRESSURE AND COLLECTING LIQUID

CROSS-REFERENCE TO RELATED APPLICATIONS

This application is a continuation of U.S. application Ser. No. 15/057,926, filed Mar. 1, 2016, which is a continuation application of U.S. application Ser. No. 12/207,841, filed Sep. 10, 2008, the entirety of each of which is hereby incorporated by reference.

BACKGROUND OF THE INVENTION

1. Field of the Invention

The present invention generally relates to an apparatus capable of preventing obstructive sleep apnea (OSA) and a method for maintaining a negative oral pressure and collecting liquid. More particularly, the present invention relates to a negative-pressure oral apparatus disposed in the oral cavity and capable of providing the oral cavity with a negative pressure to prevent obstructive sleep apnea (OSA) and snoring and expelling a liquid in the oral cavity to prevent liquid leakage or contamination and a method for maintaining a negative oral pressure and collecting liquid.

2. Description of the Prior Art

Obstructive sleep apnea (OSA) happens when the muscles in the oral cavity and the back of the gullet of a person are relaxed so that the person stops breathing intermittently for hundreds of times through the night. Each time may last as long as one minute. FIG. 1A shows the normal breathing condition of a sleeping person. In FIG. 1A, the upper respiratory airway 10 is kept unobstructed. FIG. 1B shows the muscles in the oral cavity and the back of the gullet of a person are relaxed when he is sleeping so that the upper respiratory airway 10 is narrowed to cause upper airway resistance syndrome (UARS) and snoring. In FIG. 1C, the muscles in the oral cavity and the back of the gullet of a person are relaxed when he is sleeping so that the upper respiratory airway 10 is blocked up to cause obstructive sleep apnea (OSA).

It is estimated that ten percent of the people in the world suffer from OSA. However, only a few of them are treated. Those with OSA are faced with life-threatening situations such as higher death rate, higher hypertensive risk and higher myocardial infarction (MI) risk. The survival rate of the untreated patients with apnea-hypopnea index (AHI) larger than 20 is lowered by 36 percent than the survival rate of the untreated patients with AHI smaller than 20 in eight years. The ratio of hypertension rate of the patients with respiration disorder index (RDI) of 5 to that of those people without OSA is 2:1. The ratio of hypertension rate of the patients with respiration disorder index (RDI) of 25 to that of those people without OSA is 5:1. The possibility of a recurrence of hypertension of the patients with OSA is 23 times the possibility of a recurrence of hypertension of the people without OSA. The vehicle accident rate of the untreated patient with OSA is 7 times the vehicle accident rate of the people without OSA and it is 12 times for the vehicle accident rate per mile.

Please refer to FIG. 2, which is a schematic diagram showing a constant positive airway pressure (CPAP) machine 11 used for treating OSA. The CPAP machine 11 is widely used for treating OSA by providing the patient with a constant positive airway pressure through a mask so that the upper respiratory airway is kept unobstructed. Even though the respiratory airway is kept unobstructed, it makes the patient uncomfortable because the high-pressure air flows into the upper respiratory airway. Therefore, the patient compliance rate is as low as 40 to 50%. Alternatively, OSA can also be treated by using soft tissues removal surgery, bone surgery or oral appliances.

In U.S. Pat. No. 6,494,209, an oral device for treatment of obstructive sleep disorders is disclosed. It is characterized in that the tongue is protected and separated from the teeth when the device is in use. The oral device further comprises a tongue shaped cavity for receiving the tongue. Moreover, a negative pressure is applied directly on the soft tissues of the tongue to hold the tongue within the cavity. However, such negative pressure may cause damage to the soft tissues of the tongue.

Moreover, in U.S. Pat. No. 5,957,133, an oral appliance with a negative air supply for reducing sleep apnea and snoring is provided, in which a negative air pressure source expels the air from the oral cavity to pull the tongue and the palate forward so that the upper airway is unobstructed. However, the oral appliance occupied a lot of the oral cavity and is vomitive. Meanwhile, the aforesaid patents do not teach how to effectively remove and store excess saliva.

SUMMARY OF THE INVENTION

It is one object of the present invention to provide a negative-pressure oral apparatus, capable of alleviating or curing snore and obstructive sleep apnea (OSA). The apparatus can be installed between the lips and the teeth of the user to separate the soft tissues on the lips and the tongue from the teeth and prevent the negative pressure from being applied directly on the soft tissues of the tongue.

It is another object of the present invention to provide a negative-pressure oral apparatus, capable of adjusting the position of soft tissues of the soft palate and the position of the tongue using the negative pressure so that the upper respiratory airway is kept unobstructed and the discomfort of soft tissues in the oral cavity due to the negative pressure interface is relieved.

It is still another object of the present invention to provide a negative-pressure oral apparatus and a method for maintaining a negative oral pressure and collecting liquid, the oral apparatus comprising a detachable negative-pressure element and a detachable liquid-collecting element so that the part contaminated by the saliva can be detached to be cleaned, replaced or discarded. Since the oral apparatus is tubeless, the inconvenience due to lengthy tubes can be avoided and contamination and malfunction due to saliva can be prevented, and the loading of the pump is relieved.

In one embodiment, the present invention provides a negative-pressure oral apparatus, comprising: a first gripping portion, comprising a first component and a second component having one end connected to the first component so that a first compartment is formed between the first component and the second component; and a third component, being connected to the first gripping portion so that a second compartment is formed between the third component and the second component and at least a channel is disposed between the third component and the first gripping portion.

In another embodiment, the present invention provides a negative-pressure oral apparatus, comprising: a first gripping portion, comprising a first component and a second component having one end connected to the first component so that a first compartment is formed between the first component and the second component; a third component, being connected to the first gripping portion so that a second compartment is formed between the third component and the second component and at least a channel is disposed between the third component and the first gripping portion; and a liquid collecting apparatus, being connected to the channel and capable of storing a liquid collected in the second compartment.

In another embodiment, the present invention provides a negative-pressure oral apparatus, comprising: a first gripping portion, comprising a first component and a second component having one end connected to the first component so that a first compartment is formed between the first component and the second component; a third component, being connected to the first gripping portion so that a second compartment is formed between the third component and the second component and at least a channel is disposed between the third component and the first gripping portion; and a negative-pressure element, being connected to the first gripping portion and capable of providing a negative pressure to expel gas and/or liquid in the second compartment through the channel.

In another embodiment, the present invention provides a method for maintaining a negative oral pressure and collecting liquid, comprising steps of: attaching an oral apparatus comprising a liquid collecting apparatus to a mouth of a patient; applying a negative-pressure element on an outlet of the liquid collecting apparatus so that the negative-pressure element generates a negative pressure through a channel between the liquid collecting apparatus and the oral apparatus to expel gas and/or liquid from the oral cavity and maintain the negative oral pressure; and collecting liquid by an absorbing element in the liquid collecting apparatus, while the gas is expelled through the outlet from the liquid collecting apparatus.

In another embodiment, the present invention provides a method for maintaining a negative oral pressure and collecting liquid, comprising steps of: attaching an oral apparatus comprising a negative-pressure element to a mouth of a patient; generating a negative pressure through an inlet of the negative-pressure element channeled with the oral apparatus to expel gas and/or liquid from the oral cavity and maintain the negative oral pressure; and collecting liquid by an absorbing element near the inlet of the negative-pressure element, while the gas is expelled from the absorbing element.

BRIEF DESCRIPTION OF THE DRAWINGS

The objects, spirits and advantages of the preferred embodiments of the present invention will be readily understood by the accompanying drawings and detailed descriptions, wherein.

DETAILED DESCRIPTION OF THE PREFERRED EMBODIMENT

The present invention can be exemplified by several embodiments as described hereinafter.

Figure 1A:
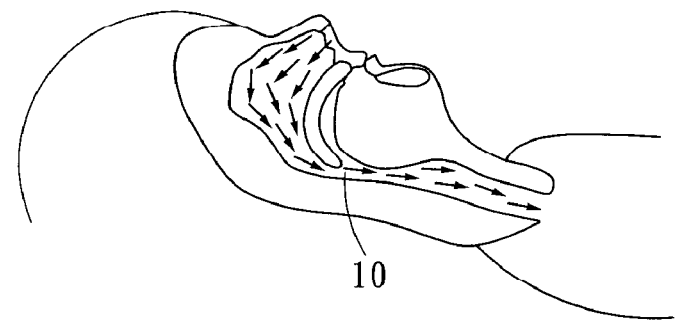
FIG. 1A to FIG. 1C show the breathing conditions of a sleeping person having a normal respiratory airway or an abnormal respiratory airway.
Figure 1B:
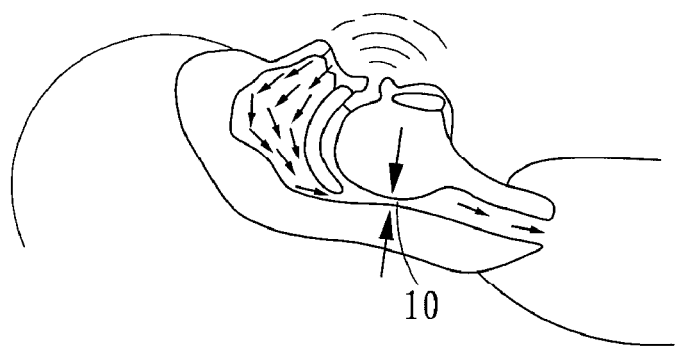
Figure 1C:
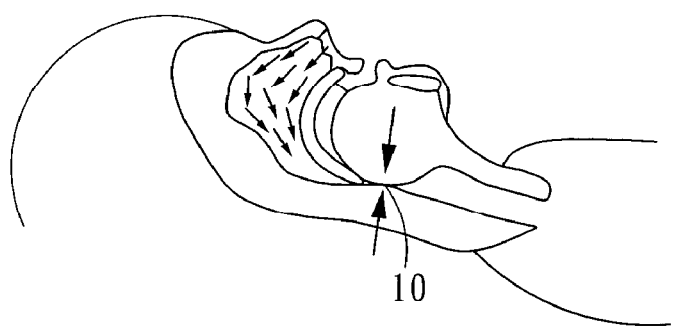
Figure 2:
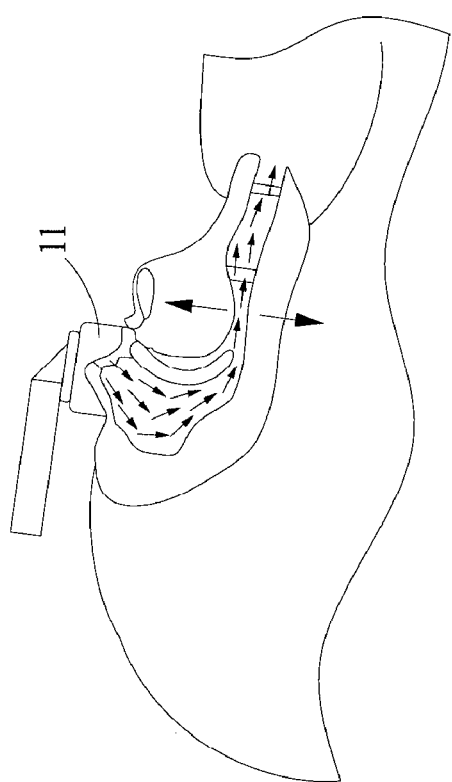
FIG. 2 is a schematic diagram showing a constant positive airway pressure (CPAP) machine 11 used for treating obstructive sleep apnea (OSA)
Figure 3A:
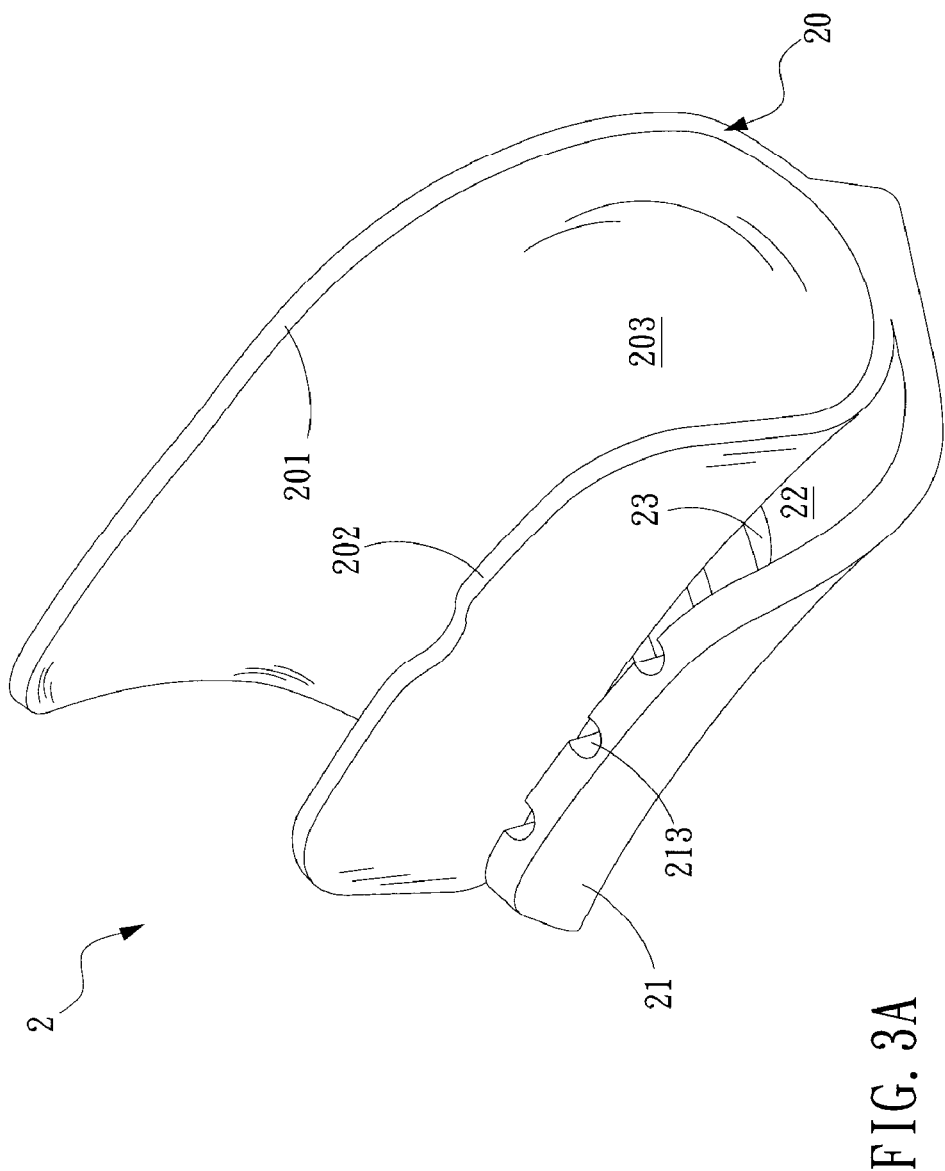
FIG. 3A is a 3-D view of a negative-pressure oral apparatus according to a first embodiment of the present invention.
Figure 3B:
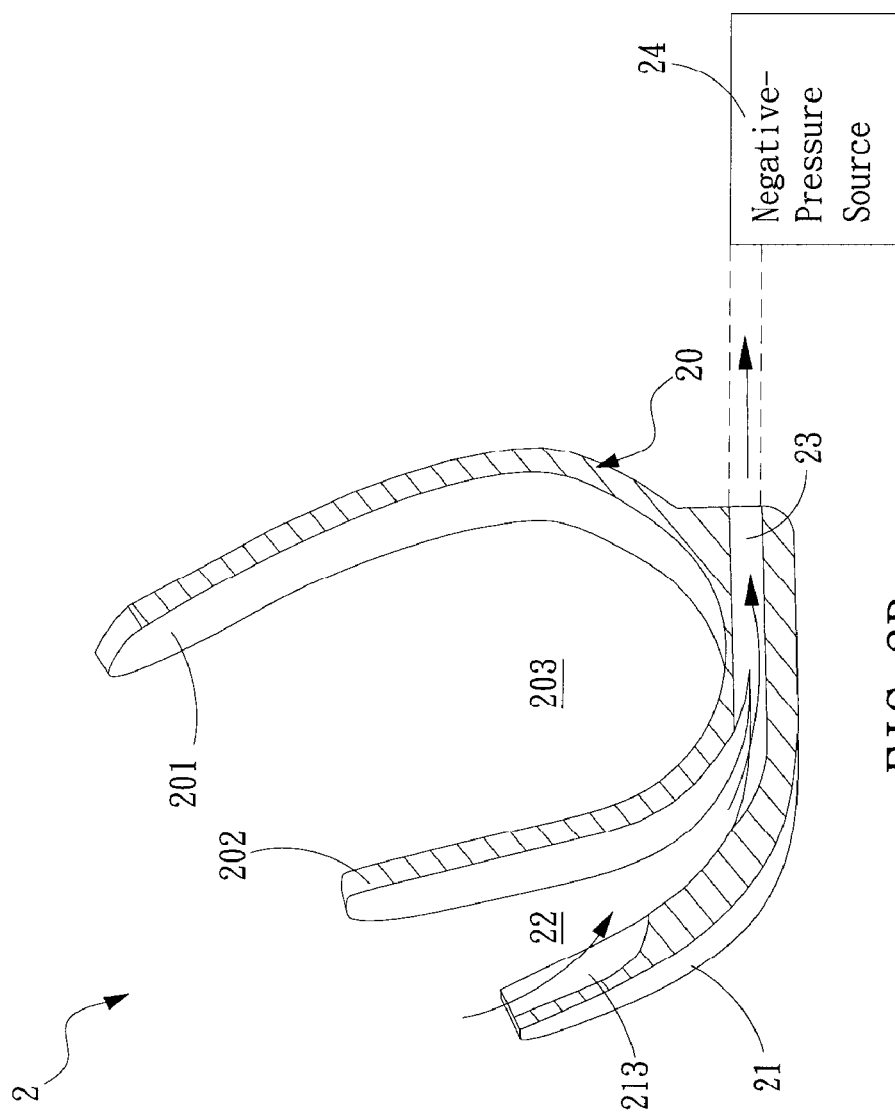
FIG. 3B is a cross-sectional view of a negative-pressure oral apparatus in FIG. 3A.

Please refer to FIG. 3A and FIG. 3B. FIG. 3A is a 3-D view of a negative-pressure oral apparatus according to a first embodiment of the present invention. FIG. 3B is a cross-sectional view of a negative-pressure oral apparatus in FIG. 3A. The negative-pressure oral apparatus 2 comprises a first gripping portion 20 and a third component 21. The first gripping portion 20 comprises a first component 201 and a second component 202. The second component 202 has one end connected to the first component 201 so that a first compartment 203 is formed between the first component 201 and the second component 202. In the present embodiment, the first component 201 is attached to the outer surface of the upper lip of the user, while the second component 202 is disposed in the oral cavity and the inner surface of the upper lip is close to the outer surface of the upper teeth.

Figure 4B:
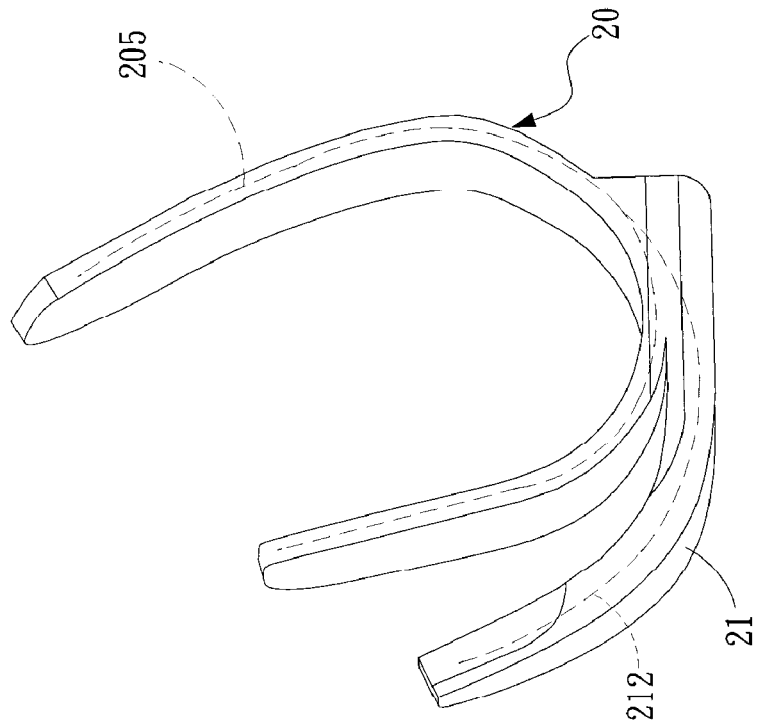
FIG. 4A and FIG. 4B are schematic diagrams of a negative-pressure oral apparatus with strengthened fixation.
Figure 4A:
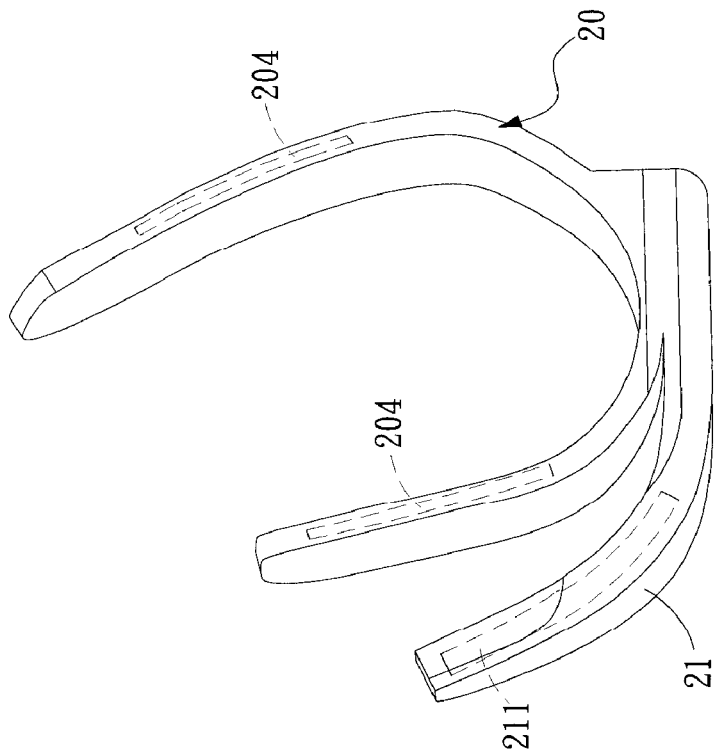

The third component 21 is coupled to the first gripping portion 20 so that a second compartment 22 is formed between the third component 21 and the second component 202. A t least a channel 23 is further disposed between the third component 21 and the first gripping portion 20. The third component 21 is disposed against the inner surface of the upper teeth and the upper gum in the oral cavity. Since the first gripping portion 20 and the third component 21 are engaged to the upper lip and the upper teeth, the negative-pressure oral apparatus 2 can be prevented from falling off due to mouth opening. In order to enhance the attachment to the oral cavity, gripping elements are embedded in the first gripping portion 20 and the third component 21, respectively, to grip the upper lip and the upper teeth. The gripping element is formed of one of an elastic material, a thermoplastic material, a magnetic material, a spring and a memory-type metal material. Please refer to FIG. 4A and FIG. 4B, which are schematic diagrams of a negative-pressure oral apparatus with strengthened fixation in another embodiment. In FIG. 4A, a gripping element 204 or 211 formed of a magnetic material is embedded in the first gripping portion 20 and the third component 21 for strengthened fixation. In FIG. 4B, a gripping element 205 or 212 formed of an elastic material, a memory-type metal material or a spring is embedded in the first gripping portion 20 and the third component 21 for strengthened fixation.

As shown in FIG. 3B in the present embodiment, the channel 23 is further coupled to a negative-pressure source 24 to provide a negative pressure. The negative-pressure source 24 can be a pump, a vacuum device or the like, which is well known to those with ordinary skills in the art. Moreover, at least a groove 213 is formed on the surface of the third component 21 corresponding to the first gripping portion 20. The groove 213 connects the external negative pressure to the oral cavity so that the soft palate and the surrounding soft tissues of the user are pulled towards the front portion of the oral cavity and the tongue is pulled towards the upper palate to keep the upper respiratory airway unobstructed.

Figure 5A:
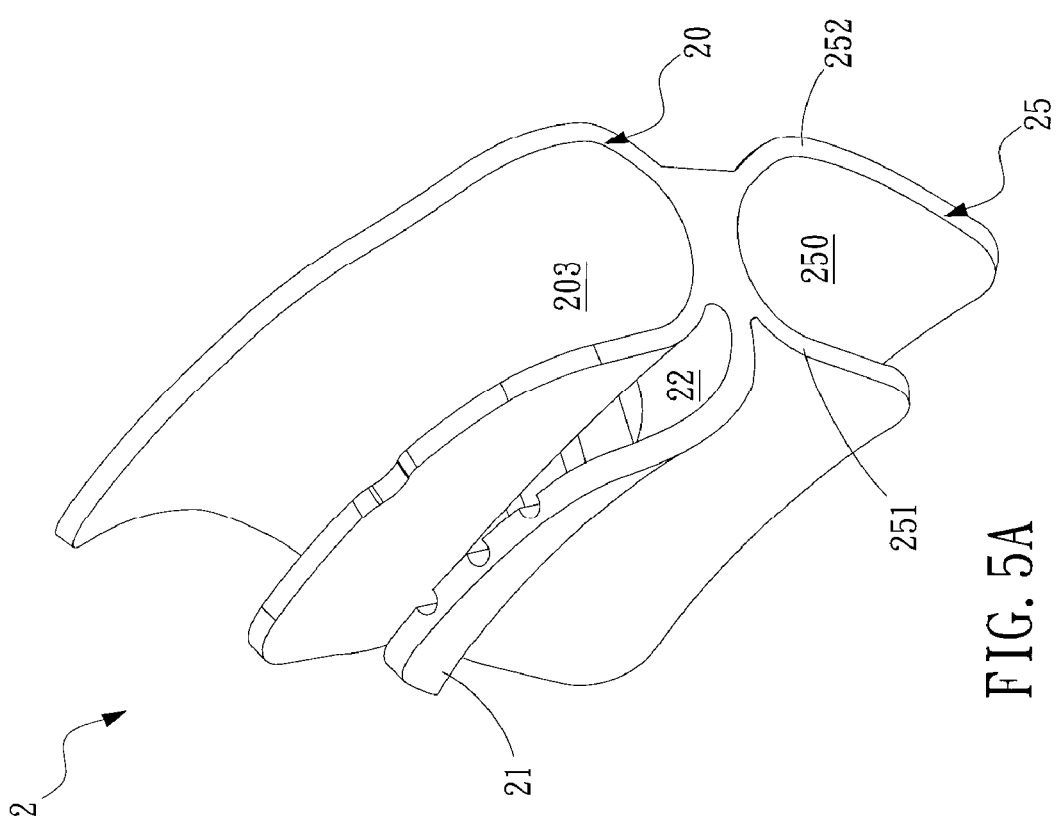
FIG. 5A and FIG. 5B show a 3-D view and a cross-sectional view of a negative-pressure oral apparatus according to a second embodiment of the present invention.
Figure 5B:
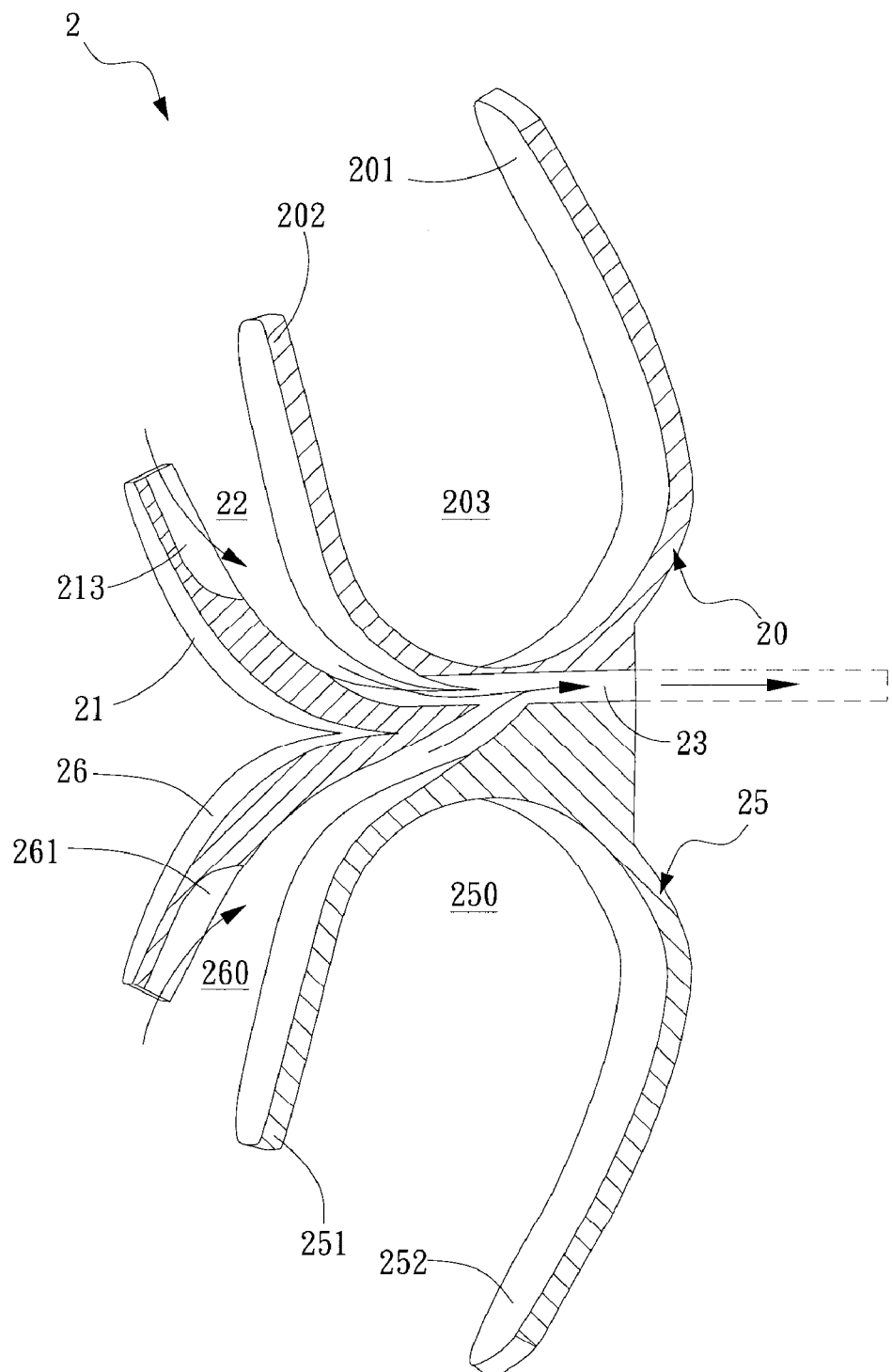
Figure 5C:
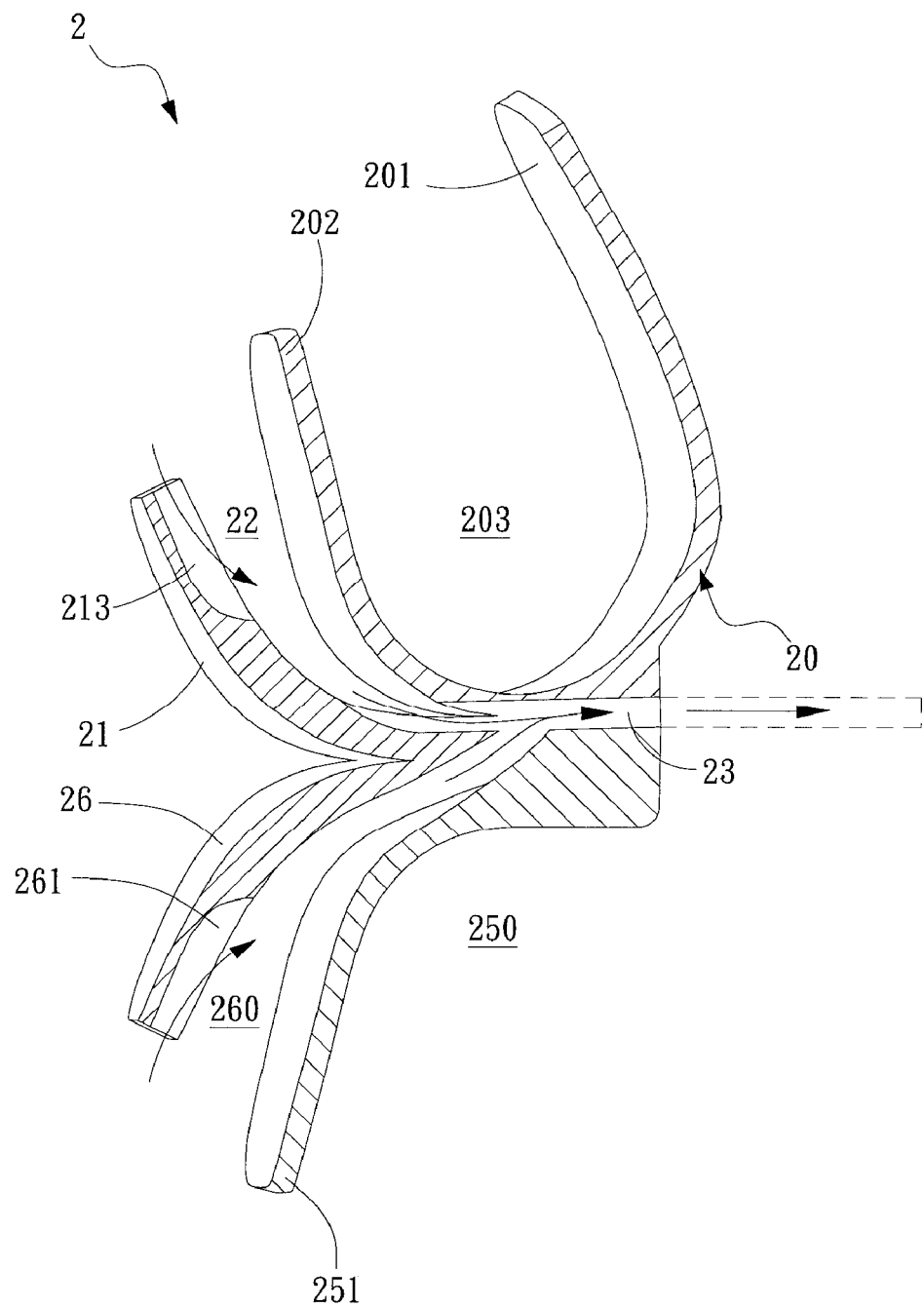
FIG. 5C is a cross-sectional view of a negative-pressure oral apparatus without a sixth component according to a second embodiment of the present invention.

Please refer to FIG. 5A, which shows a 3-D view of a negative-pressure oral apparatus according to a second embodiment of the present invention. In the present embodiment, the negative-pressure oral apparatus 2 is similar to that in the first embodiment except that the oral apparatus 2 further comprises a second gripping portion 25, which is similar to the first gripping portion 20 in structure. The second gripping portion 25 comprises a fifth component 251 and a sixth component 252 to form a third compartment 250 therein so that the second gripping portion 25 is attached to the bottom lip of the user to further facilitate the fixation between the oral apparatus 2 and the oral cavity of the user. As shown in FIG. 5B, a fourth component 26 is further provided to be coupled to the second gripping portion 25. More particularly, a fourth compartment 260, channeled with the channel 23, is formed between the fourth component 26 and the fifth component 251. The fourth component 26 is disposed against the inner surface of the bottom teeth and the bottom gum in the oral cavity. Moreover, the fourth component 26 further comprises at least a groove 261, which is functionally similar to the groove 213, and thus description thereof is not presented. As shown in FIG. 5C, the second embodiment can do without the sixth component 252 of the second gripping portion 25, but further comprise a compartment 260 formed between the fourth component 26 and the fifth component 251. The compartment 260 can be channeled with the channel 23. The second gripping portion 25 and the fourth component 26 can be formed of an elastic material or a thermoplastic material. Alternatively, as shown in FIG. 4A or FIG. 4B, a gripping element formed of an elastic material, a memory-type material, a spring or a magnetic material can be embedded to strengthen fixation.

Figure 6A:
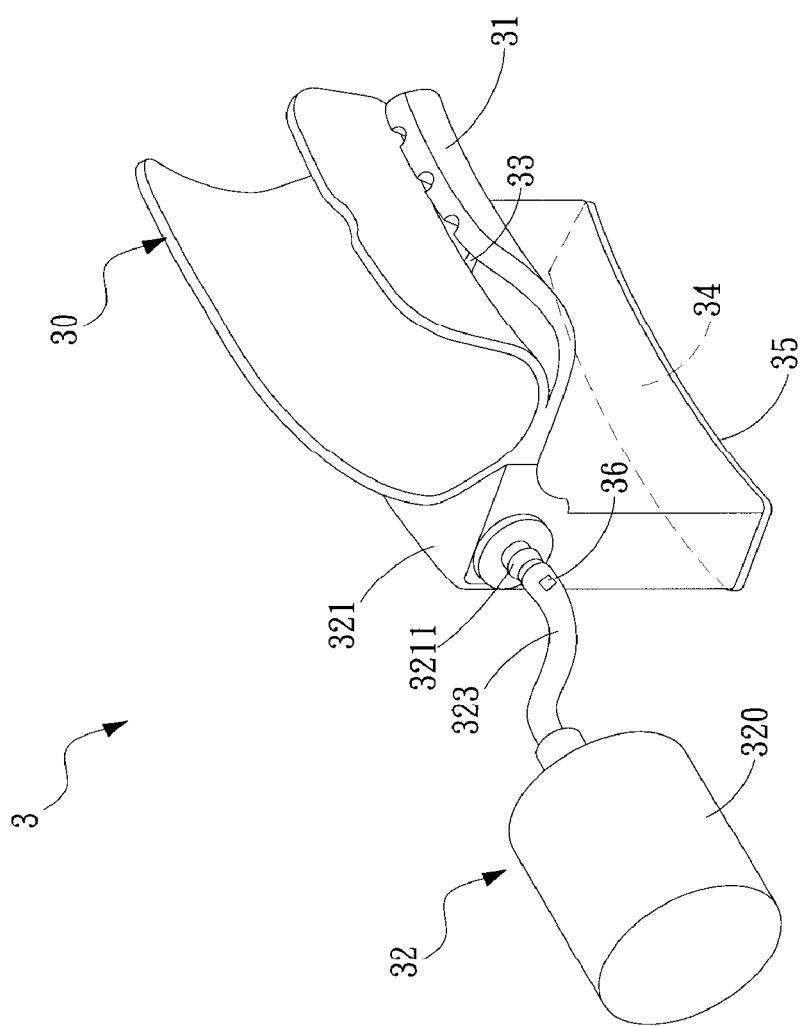
FIG. 6A is a 3-D view of a negative-pressure oral apparatus according to a third embodiment of the present invention.
Figure 6B:
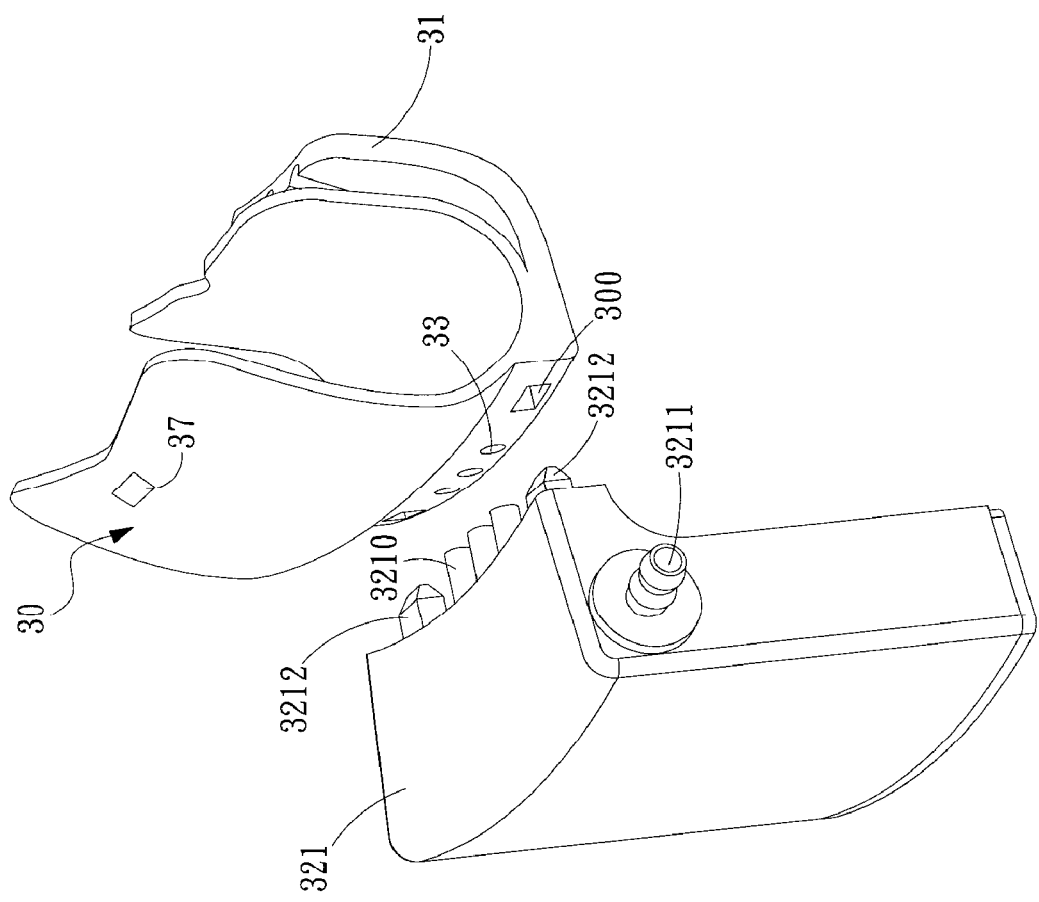
FIG. 6B is an exploded view of a negative-pressure oral apparatus in FIG. 6A.

Please refer to FIG. 6A, which is a 3-D view of a negative-pressure oral apparatus according to a third embodiment of the present invention. The negative-pressure oral apparatus 3 comprises a first gripping portion 30, a third component 31 and a liquid collecting apparatus 32. The first gripping portion 30 and the third component 31 are structured as described in the first embodiment, and thus the descriptions thereof are not presented. The liquid collecting apparatus 32 is connected with the compartment between the third component 31 and the first gripping portion 30 via at least a channel 33. The liquid collecting apparatus 32 is capable of sucking liquid from the compartment between the third component 31 and the first gripping portion 30. The liquid collecting apparatus 32 comprises a container 321 and a negative-pressure element 320. The liquid collecting apparatus 32 comprises an opening 34 and a sealing cap 35 at the bottom portion for internal cleaning. As shown in FIG. 6B, which is an exploded view of a negative-pressure oral apparatus in FIG. 6A. The container 321 comprises at least an inlet 3210 and an outlet 3211. The inlet 3210 is connected with the channel 33 on the first gripping portion 20 to collect saliva in the oral cavity. In order to attach the container 321 firmly to the first gripping portion 30, the container 321 further comprises at least a connecting member 3212 to be combined with a complementary connecting member 300 on the first gripping portion 30 so that the first gripping portion 30 and the container 321 can be securely attached to prevent leakage of gas/liquid. Moreover, the connecting member 3212 is designed so that the container 321 and the first gripping portion 30 can be easily disassembled to provide portability and convenience for the user to carry, clean and maintain.

Figure 6C:
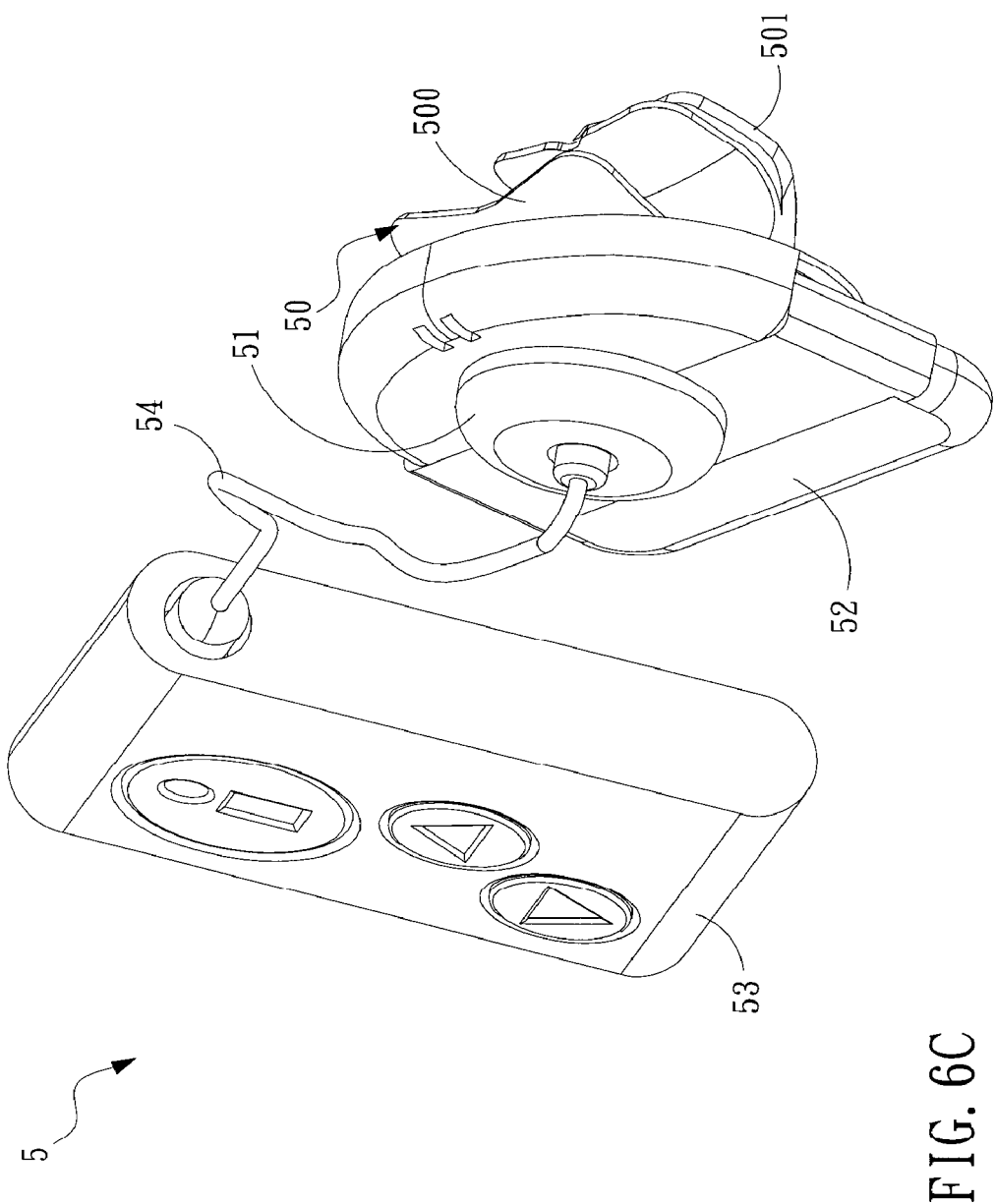
FIG. 6C is a 3-D view of a negative-pressure oral apparatus according to a fourth embodiment of the present invention.

Please refer to FIG. 6C, which is a 3-D view of a negative-pressure oral apparatus according to a fourth embodiment of the present invention. In the present embodiment, the negative-pressure oral apparatus 5 comprises a body 50, a negative-pressure pump 51, a liquid collector 52 and a control unit 53. The body 50 comprises a first gripping portion 500 and the third component 501, as described in the first embodiment. The negative-pressure pump 51 is connected with a channel (not shown but exemplified by label 23 in FIG. 3B) in the body 50 to provide negative pressure to suck fluid from the oral cavity through the channel into the liquid collector 52, which is also channeled with the negative-pressure pump 51. The control unit 53 is electrically connected to the negative-pressure pump 51 via an electrical wire 54 to control the negative-pressure pump. The embodiment in FIG. 6C is similar to the embodiment in FIG. 6A except that the liquid collector 52 in FIG. 6C is integrated with the negative-pressure pump 51 and is connected to the body 50 through the negative-pressure pump 51.

Figure 7:
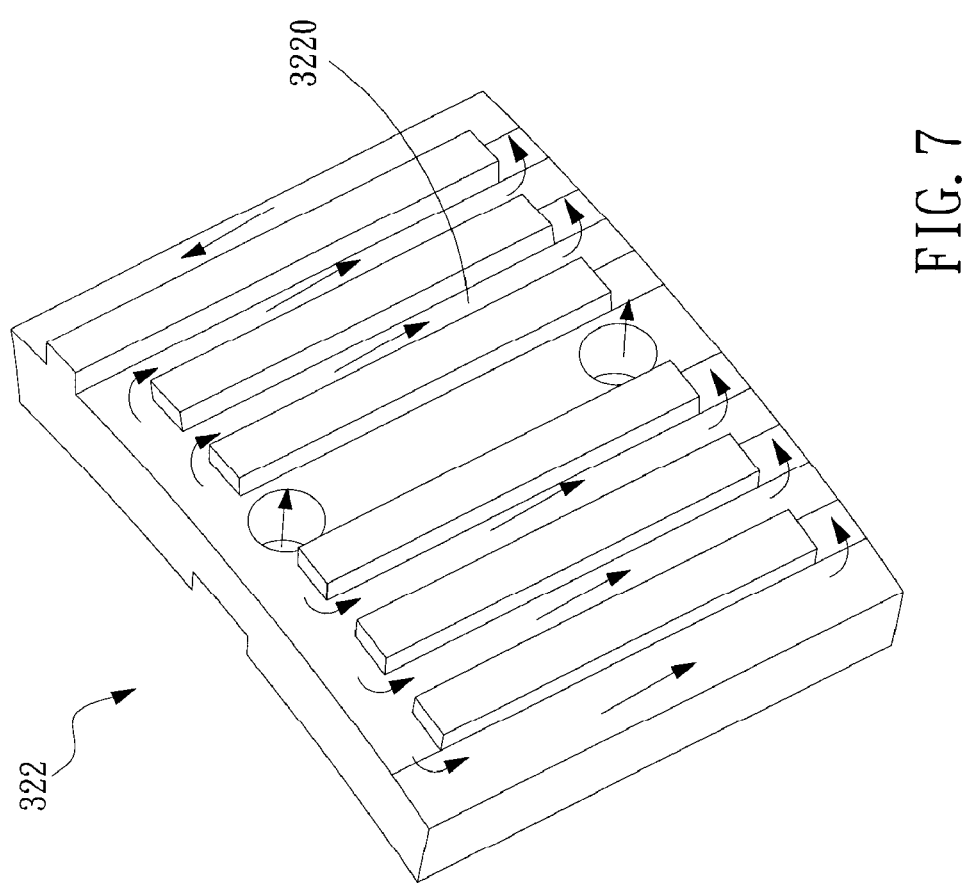
FIG. 7 is a schematic diagram of an absorbing element of the present invention.

Please refer to FIG. 7, which is a schematic diagram of an absorbing element of the present invention. The container 321 comprises an absorbing element 322 to absorb liquid from the inlet. Referring to FIG. 6A and FIG. 7, the absorbing element 322 can be inserted into the liquid collecting apparatus 32 via the opening 34, which is then sealed by the sealing cap 35. Generally, the absorbing element 322 is formed of a absorbent material or a porous material, such as sponge, paper, cloth, foam, absorptive resin or the like. However, the present invention is not limited thereto. The absorbing element 322a is capable of absorbing liquid. On the other hand, the absorbing element 322a is porous to provide a negative-pressure gas flow. Moreover, the absorbing element 322 is removable, re-usable or disposable, and thus can be replaced or discarded according to practical usage to keep the oral apparatus 3 clean. In the present embodiment, the absorbing element 322 further comprises a winded channel 3220 to increase the probability that the liquid expelled (such as saliva) is absorbed by the absorbing element 322 and to allow the gas to flow through quickly. Returning to FIG. 6A, the negative-pressure element 320 is a removable micro-pump attached to the oral apparatus 3. The negative-pressure element 320 is coupled to the outlet 3211 through the tube 323 or is tubelessly coupled to the outlet 3211. The negative-pressure element 320 is capable of providing a negative pressure so that the gas and/or liquid between the third component 31 and the first gripping portion 30 is pumped into the container 321. Using such design of the absorbing element and the negative-pressure element, problems due to contamination caused by saliva can be prevented.

As shown in FIG. 6A, FIG. 6B and FIG. 7, the present invention further provides a method for maintaining a negative oral pressure and collecting liquid, comprising steps of:

attaching an oral apparatus 3 comprising a liquid collecting apparatus 32 to a mouth of a patient; applying a negative-pressure element 320 on an outlet 3211 of the liquid collecting apparatus 32a so that the negative-pressure element 320 generates a negative pressure through a channel 33 between the liquid collecting apparatus 32 and the oral apparatus 3 to expel gas and/or liquid from the oral cavity and maintain the negative oral pressure; and collecting liquid by an absorbing element 322 in the liquid collecting apparatus 32, while the gas is expelled through the outlet 3211 from the liquid collecting apparatus 32. Moreover, the method further comprises steps of: using a pressure sensor unit 36 to sense the pressure in the oral cavity after the negative-pressure element 320 is started; and turning off the negative-pressure element 320 automatically if the negative-pressure element 320 has been running for a period of time while the oral pressure does not reach its target value, which indicates that the oral apparatus 3 is not installed properly and may have leakage. Moreover, the pressure sensor unit 36 is capable of sensing the pressure in the oral cavity when the negative-pressure element 320 is not running; when the patient sucks voluntarily and man-made negative pressure in the oral cavity can be used as a triggering signal to start the negative-pressure element 320 automatically. Moreover, the method further comprises steps of: using a flow sensor unit 37 to sense the breathing air flow of the patient when the negative-pressure element 320 is started; and turning off the negative-pressure element 320 automatically if the breath is not sensed for a period of time.

Figure 8A:
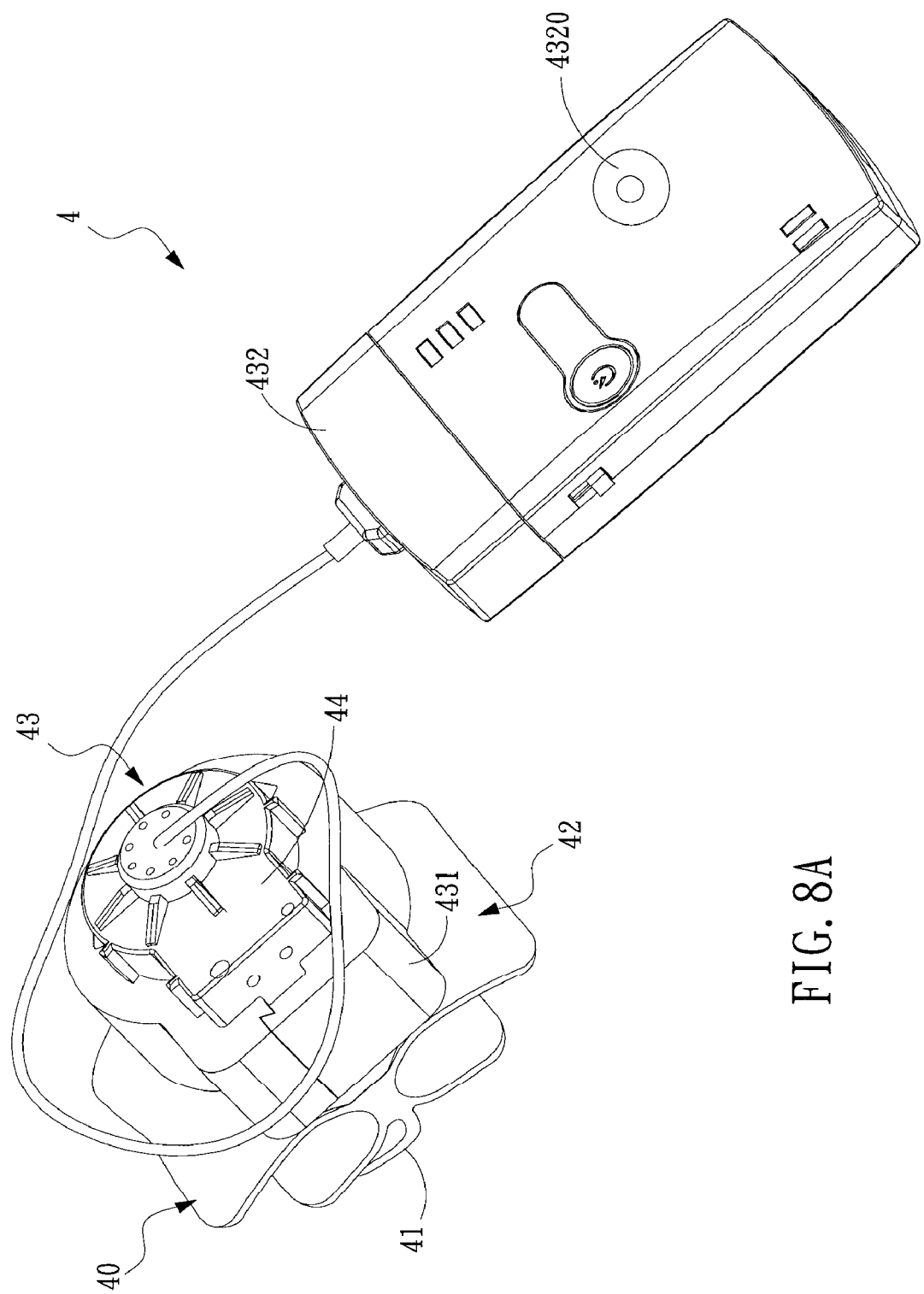
FIG. 8A is a 3-D view of a negative-pressure oral apparatus according to a fifth embodiment of the present invention.
Figure 8B:
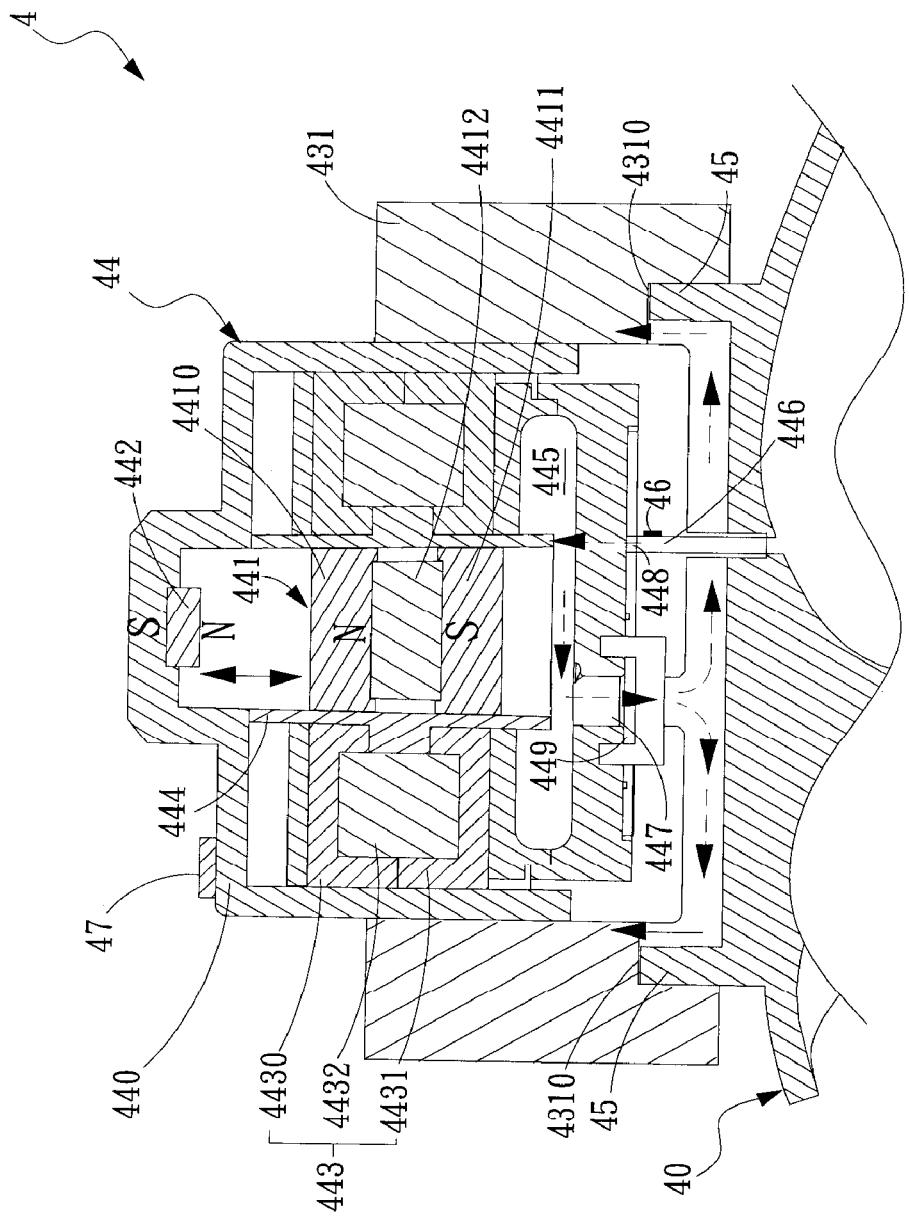
FIG. 8B is a cross-sectional view of a liquid collecting apparatus of the present invention.

Please refer to FIG. 8A and FIG. 8B. More particularly, FIG. 8A is a 3-D view of a negative-pressure oral apparatus according to a fifth embodiment of the present invention; and FIG. 8B is a cross-sectional view of a liquid collecting apparatus of the present invention. In the present embodiment, the oral apparatus 4 comprises a first gripping portion 40, a third component 41, a second gripping portion 42 and a liquid collecting apparatus 43. The first gripping portion 40, the third component 41 and the second gripping portion 42 are structured as previously described and thus descriptions thereof are not repeated. In the present embodiment, the liquid collecting apparatus 43 comprises a pumping element 44, an absorbing element 431 and a control unit 432. The pumping element 44 comprises an inlet 446 and an outlet 447. The inlet 446 is connected with at least a channel (not shown but exemplified by label 23 in FIG. 3B) to suck gas and/or liquid and drain gas and/or liquid through the outlet 447. The absorbing element 431 is coupled to the outlet 447 to absorb the liquid from the outlet 447. The absorbing element 431 further comprises a hollow recessed part 4310 to embed the pumping element 44 and a protruding part 45 on the first gripping portion 40 so that the absorbing element 431 and the oral apparatus 4 are detachably connected to enable the user to replace the absorbing element 431 or to separate the absorbing element 431 and the pumping element 44 for cleaning according to usage conditions. The control unit 432 is electrically connected to the pumping element 44. In the present embodiment, the control unit 432 controls the power module to provide the pumping element 44 with AC signals. The absorbing element 431 is structured as previously described and thus description thereof is not repeated.

Moreover, the inlet 446 further comprises a pressure sensor unit 46 electrically connected to the control unit 432. The pressure sensor unit 46 is capable of sensing the pressure in the oral cavity after the pumping element 44 is activated. The control unit 432 turns off the pumping element 44 automatically or an alarm unit 4320 issues an alarm signal if the pumping element 44 has been operated for a period of time while the sensed oral pressure does not reach its target value, which indicates that the oral apparatus 3 is not installed properly and may have leakage. Moreover, the pressure sensor unit 46 is capable of sensing the pressure in the oral cavity when the pumping element 44 is not started. The control unit 432 turns on the pumping element 44 automatically when the pressure is lowered by the man-made oral suction of the patient. When the pumping element 44 is activated, the negative pressure caused by the pumping element 44 pulls the soft palate and the surrounding soft tissues of the user towards the front portion of the oral cavity and the tongue towards the upper palate to keep the upper respiratory airway of the user unobstructed. Moreover, the oral apparatus 4 further comprises a flow sensor unit 47 electrically connected to the control unit 432. The flow sensor unit 47 is capable of sensing the breathing flow of the user when the pumping element 44 is running so that the control unit 432 turns off the pumping element 44 automatically and the alarm unit 4320 issues an alarm signal if the breathing flow is not sensed for a period of time.

The pumping element 44 comprises a casing 440, a piston 441, a thrust generator 442 and a winding portion 443. The casing 40 further comprises a cylinder 444 therein to install the piston 441. The piston 441 comprises a permanent magnetic field that is capable of performing movement in the cylinder 444. In the present embodiment, the piston 441 further comprises a pair of magnetically permeable caps 4410 and 4411 and a magnetic body 4412. The magnetic body 4412 is disposed between the pair of magnetically permeable caps 4410 and 4411 to provide the permanent magnetic field. In the present embodiment, the magnetic body 442 is a permanent magnet. The end of the magnetic body 442 corresponding to the casing 440 is the northern pole, while the other end of the magnetic body 442 is the southern pole.

The thrust generator 442 is disposed on an inner wall of the casing 440 and is facing the piston 441. In the present embodiment, the thrust generator 442 is a magnetic element, which is capable of providing a magnetic field having a direction opposite to magnetic field direction of the magnetic body 4412 so that a first action force is generated on the piston 441. The winding portion 443 is disposed on one side of the cylinder 444, to provide a second action force on the piston 441 to move the piston 441. Therefore, the piston 441 can move up and down in the cylinder 444 due to the resultant of the second action force and the first action force. In the present embodiment, the winding portion 443 further comprises a top magnetic ring 4430, a bottom magnetic ring 4431 and a coil 4432. The coil 4432 is disposed in the compartment between the top magnetic ring 4430 and the bottom magnetic ring 4431. The coil 4432 generates the second action force after it is fed with electrical signals. The cylinder 444 is further connected with a compression chamber 445. The compression chamber 445 is coupled to the inlet and the outlet. Furthermore, a check valve 448 is disposed between the inlet 446 and the compression chamber 445, and a check valve 449 is disposed between the outlet 447 and the compression chamber 445.

When the coil 4431 is not fed with electrical signals, a rejection force is generated between the piston 441 and the thrust generator 442 if the thrust generator 442 and the piston 441 faces with the same magnetic pole (for, example, the northern pole in the present embodiment) so that the piston 441 is departed from the center of the coil 4431. When the coil 4431 is fed with an AC electrical signal, a reversed magnetic force is generated from the winding portion 443 to push the piston 441 out if the phase of the AC electrical signal is negative. On the contrary, a forward magnetic force is generated from the winding portion 443 to overcome the rejection force between the piston 441 and the thrust generator 442 to pull the piston 441 in if the phase of the AC electrical signal is positive. In this manner, with the repeatedly alternative positive and negative potentials, the resultant of the magnetic force generated from the winding portion 443 and the rejection force generated from the thrust generator 442 enables the piston 441 to move up and down in the cylinder 444. As the piston 441 moves upwards in the cylinder 444, a negative pressure is generated so that saliva is expelled via the channel between the third component 41 and the first gripping portion 40 to pass through the inlet 446 to enter the compression chamber 445. As the piston 441 moves downwards in the cylinder 444, a positive pressure is generated to push saliva through the outlet 447 to enter the absorbing element 431.

Using the apparatus as shown in FIG. 8A and FIG. 8B, the present invention provides a tubeless method for maintaining a negative oral pressure and collecting liquid, comprising steps of: attaching an oral apparatus 4 comprising a negative-pressure element to a mouth of a patient; generating a negative pressure through an inlet of the negative-pressure element connected with the oral apparatus 4 to expel gas and/or liquid from the oral cavity and maintain the negative oral pressure; and collecting liquid by an absorbing element 431 near the inlet of the negative-pressure element, while the gas is expelled from the absorbing element 431. In the present embodiment, the negative-pressure element is a micro pumping element 44 capable of generating a negative pressure. Moreover, the method further comprises steps of: using a pressure sensor unit 46 to sense the pressure in the oral cavity after the pumping element 44 is started; and turning off the pumping element 44 automatically if the pumping element 44 has been operated for a period of time while the sensed oral pressure does not reach its target value, which indicates that the oral apparatus 3 is not installed properly and may have leakage. Moreover, the pressure sensor unit 46 is capable of sensing the pressure in the oral cavity when the pumping element 44 is not started so that the pumping element 44 can be turned on automatically when the oral cavity pressure of the patient is lowered by man-made suction. Moreover, the method further comprises steps of: using a flow sensor unit 47 to sense the breathing flow of the patient when the pumping element 44 is started; and turning off the pumping element 44 automatically if the breathing flow is not sensed for a period of time.

In the present invention, the liquid collecting apparatus and the gripping portion can be modified and combined. However, any person with ordinary skill in the art is able to make modifications within the scope of the present invention. Moreover, the negative-pressure source 24 in FIG. 3B and the negative-pressure element 320 in FIG. 6A can be replaced by the pumping element 44 in FIG. 8B.

Accordingly, the present invention discloses a negative-pressure oral apparatus disposed in the oral cavity and capable of providing the oral cavity with a negative pressure to prevent obstructive sleep apnea (OSA) and snoring and expelling a liquid in the oral cavity while preventing saliva leakage or contamination and a method for maintaining a negative oral pressure and collecting liquid. Therefore, the present invention is novel, useful and non-obvious.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A negative-pressure oral apparatus for alleviating snoring and obstructive sleep apnea of a user, comprising:
    an oral interface insertable in an oral cavity of the user, wherein the oral interface defines a fluid passage configured to be in fluid communication with the oral cavity of the user when the oral interface is inserted in the oral cavity of the user;
    a source of negative pressure in fluid communication with the fluid passage of the oral interface, wherein the source of negative pressure is configured to generate negative pressure within the oral cavity of the user via the oral interface in use;
    a liquid-collecting container in fluid communication with the passage of the oral interface and the source of negative pressure; and
    a control unit in electrical communication with the source of negative pressure, wherein the control unit is configured to control operation of the source of negative pressure,
    wherein the oral interface, the source of negative pressure, and the control unit are operable to draw a soft palate of the user forward toward the front of the oral cavity in use,
    wherein the liquid-collecting container is configured to receive and collect saliva drawn into the container from the oral cavity of the user in use,
    wherein the liquid-collecting container is downstream of the oral interface and upstream of the source of negative pressure.

2. The negative-pressure oral apparatus set forth in claim 1, further comprising a flow sensor in electrical communication with the control unit, the flow sensor configured to sense breathing air flow from the user and generate an electrical flow signal indicative of sensed breathing air flow from the user during operation of the source of negative pressure in use.

3. The negative-pressure oral apparatus set forth in claim 2, wherein the control unit is configured to receive the electrical flow signal from the flow sensor and analyze the received electrical flow signal to determine if the received electrical flow signal is indicative of the patient not breathing.

4. The negative-pressure oral apparatus set forth in claim 3, wherein the control unit is configured to determine the received electrical flow sensor is indicative of the patient not breathing if the electrical flow signal indicates no breathing air flow for a predetermined period of time.

5. The negative-pressure oral apparatus set forth in claim 4, wherein the control unit is configured to deactivate the source of negative pressure if the control unit determines that the patient is not breathing.

6. The negative-pressure oral apparatus set forth in claim 5, further comprising an alarm unit in electrical communication with the control unit, the alarm unit configured to issue an alarm signal to the user, wherein the control unit is configured to activate the alarm unit if the control unit determines that the patient is not breathing.

7. The negative-pressure oral apparatus set forth in claim 1, further comprising a pressure sensor in electrical communication with the control unit, the pressure sensor configured to sense pressure in the oral cavity of the user and generate an electrical pressure signal to the control unit indicative of the pressure in the oral cavity of the user during operation of the source of negative pressure in use.

8. The negative-pressure oral apparatus set forth in claim 7, wherein the control unit is configured to receive the electrical pressure signal from the pressure sensor and analyze the received electrical pressure signal to determine if the received electrical pressure signal is indicative of the pressure in the oral cavity reaching a predetermined target pressure.

9. The negative-pressure oral apparatus set forth in claim 8, wherein the control unit is configured to determine whether the pressure in the oral cavity has reached the predetermined target pressure within a predetermined period of time based on the received electrical pressure signal.

10. The negative-pressure oral apparatus set forth in claim 8, wherein the control unit is configured to deactivate the source of negative pressure if the control unit determines that the pressure in the oral cavity has not reached the predetermined target pressure within a predetermined period of time.

11. The negative-pressure oral apparatus set forth in claim 8, further comprising an alarm unit in electrical communication with the control unit, the alarm unit configured to issue an alarm signal to the user, wherein the control unit is configured to activate the alarm unit if the control unit determines that the pressure in the oral cavity has not reached the predetermined target pressure within a predetermined period of time.

12. The negative-pressure oral apparatus set forth in claim 1, further comprising a pressure sensor in electrical communication with the control unit, the pressure sensor configured to sense pressure in the oral cavity the user and generate an electrical pressure signal indicative of the pressure in the oral cavity of the user during non-operation of the source of negative pressure in use.

13. The negative-pressure oral apparatus set forth in claim 12, wherein the control unit is configured to receive the electrical pressure signal from the pressure sensor and analyze the received electrical pressure signal to determine if the received electrical pressure signal is indicative of the pressure in the oral cavity lowered by oral suction by the patient.

14. The negative-pressure oral apparatus set forth in claim 13, wherein the control unit is configured to activate the source of negative pressure if the control unit determines that the pressure in the oral cavity lowered by oral suction by the patient.

15. The negative-pressure oral apparatus set forth in claim 1, wherein the source of negative pressure is a vacuum pump.

16. The negative-pressure oral apparatus set forth in claim 1, further comprising an alarm unit in electrical communication with the control unit.

17. The negative-pressure oral apparatus set forth in claim 1, wherein the source of negative pressure comprises:
   a casing;
   a cylinder disposed in the casing;
   a piston disposed in the cylinder and configured to move therein, the piston providing a permanent magnetic field;
   a thrust generator disposed in the casing and facing the piston, the thrust generator being capable of generating a first action magnetic force on the piston; and
   a winding portion disposed on one side of the cylinder, the winding portion being capable of providing a second action magnetic force on the piston to move the piston.

18. The negative-pressure oral apparatus set forth in claim 17, wherein the thrust generator is a magnetic element including two ends having the same magnetic pole, wherein one end of the magnetic element faces one end of the piston.

19. The negative-pressure oral apparatus as recited in claim 18, wherein the piston further comprises:
   a pair of magnetically permeable caps; and
   a magnetic body disposed between the pair of magnetically permeable caps to provide the permanent magnetic field.

20. The negative-pressure oral apparatus as recited in claim 18, wherein the winding portion further comprises:
   a magnetic ring including a compartment to contain the cylinder therein; and
   a coil disposed in the compartment of the magnetic ring, the coil being capable of providing the second action force.

21. The negative-pressure oral apparatus as recited in claim 17, wherein the winding portion is configured to receive an AC electrical signal to generate alternating positive and negative second action magnetic forces, wherein the alternating positive and negative second action magnetic forces and the first action magnetic force cause the piston to reciprocate in the cylinder.

22. The negative-pressure oral apparatus as recited in claim 21, wherein the source of negative pressure further comprises a compression chamber fluidly connected between the oral interface and the liquid-collecting container, wherein the piston generates negative pressure in the compression chamber when the piston moves in a first direction in the cylinder to draw saliva from the oral interface into the compression chamber, wherein the piston generates a positive pressure in the compression chamber when the piston moves in a second direction in the cylinder to push the saliva in the compression chamber toward the liquid-collecting chamber.

23. A method of using the negative-pressure oral apparatus set forth in claim 1, the method comprising:
   inserting the oral interface into the oral cavity of the user, wherein the fluid passage of the oral interface is in fluid communication with the oral cavity of the user; and
   activating the source of negative pressure in fluid communication with the fluid passage via the control unit in electrical communication with the source of negative pressure to draw a vacuum in the oral cavity of the user and pull a soft palate of the user forward toward a front portion of the oral cavity.

24. The method of using the negative-pressure oral apparatus set forth in claim 1 further comprising drawing saliva, simultaneously with said drawing a vacuum, from the oral cavity through the fluid passage and into a liquid container.

25. A method of alleviating snoring and obstructive sleep apnea of a user, the method comprising:
   inserting an oral interface into an oral cavity of the user, wherein a fluid passage of the oral interface is in fluid communication with the oral cavity of the user;
   activating a source of negative pressure in fluid communication with the fluid passage via a control unit in electrical communication with the source of negative pressure to draw a vacuum in the oral cavity of the user and pull a soft palate of the user forward toward a front portion of the oral cavity;
   drawing saliva, simultaneously with said drawing a vacuum, from the oral cavity through the fluid passage and into a liquid container;
   sensing, via a flow sensor in electrical communication with the control unit, breathing air flow from the user during said activating a source of negative pressure;

generating, via the flow sensor, an electrical flow signal indicative of the sensed breathing air flow of the user; and receiving, at the control unit, the electrical flow signal.

26. The method of alleviating snoring and obstructive sleep apnea of a user set forth in claim 25, further comprising:

sensing, via a pressure sensor in electrical communication with the control unit, pressure in the oral cavity of the user during said activating a source of negative pressure;

generating, via the pressure sensor, an electrical pressure signal indicative of the pressure in the oral cavity of the user; and receiving, at the control unit, the electrical pressure signal.

27. The method of alleviating snoring and obstructive sleep apnea of a user set forth in claim 25, further comprising:

sensing, via a pressure sensor in electrical communication with the control unit, pressure in the oral cavity of the user before said activating a source of negative pressure;

generating, via the pressure sensor, an electrical pressure signal indicative of the pressure in the oral cavity of the user; and receiving, at the control unit, the electrical pressure signal.

* * * * *